United States Patent
Kim et al.

(10) Patent No.: US 11,511,624 B2
(45) Date of Patent: Nov. 29, 2022

(54) APPARATUS AND METHOD FOR MEASURING ALCOHOL CONCENTRATION, AND SYSTEM FOR CONTROLLING STARTING OF VEHICLE

(71) Applicants: Hyundai Motor Company, Seoul (KR); Kia Motors Corporation, Seoul (KR)

(72) Inventors: Dong Gu Kim, Gyeonggi-do (KR); Sang Hyeok Yang, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 683 days.

(21) Appl. No.: 16/554,282

(22) Filed: Aug. 28, 2019

(65) Prior Publication Data
US 2020/0317052 A1    Oct. 8, 2020

(30) Foreign Application Priority Data

Apr. 5, 2019 (KR) .................. 10-2019-0040256

(51) Int. Cl.
| | |
|---|---|
| *B60K 28/06* | (2006.01) |
| *A61B 5/1455* | (2006.01) |
| *A61B 5/00* | (2006.01) |
| *A61B 5/145* | (2006.01) |
| *A61B 5/18* | (2006.01) |
| *A61B 5/1171* | (2016.01) |

(52) U.S. Cl.
CPC .......... *B60K 28/063* (2013.01); *A61B 5/1171* (2016.02); *A61B 5/1455* (2013.01); *A61B 5/14532* (2013.01); *A61B 5/14546* (2013.01); *A61B 5/18* (2013.01); *A61B 5/489* (2013.01); *A61B 5/4845* (2013.01); *A61B 5/6893* (2013.01); *A61B 5/7225* (2013.01)

(58) Field of Classification Search
CPC ... A61B 5/0205; A61B 5/0059; A61B 5/1455; A61B 5/14551; A61B 5/14552; A61B 5/14532; A61B 5/14546; A61B 5/4845; A61B 5/6893; A61B 5/6826; A61B 5/7225; A61B 5/18; A61B 5/1171; A61B 5/489
See application file for complete search history.

(56) References Cited

U.S. PATENT DOCUMENTS

| | | | | |
|---|---|---|---|---|
| 2003/0090154 | A1* | 5/2003 | Takezaki | B60R 25/25 307/10.2 |
| 2007/0200663 | A1* | 8/2007 | White | A61B 5/14546 340/5.31 |
| 2011/0228397 | A1* | 9/2011 | Matsushita | G02B 26/001 359/578 |

FOREIGN PATENT DOCUMENTS

KR    100816249 B1    3/2008

* cited by examiner

*Primary Examiner* — Chu Chuan Liu
(74) *Attorney, Agent, or Firm* — Fox Rothschild LLP

(57) ABSTRACT

In a method and apparatus for measuring an alcohol concentration, a blood alcohol concentration of a driver is rapidly and precisely measured by selecting a plurality of wavelengths based on the absorbance for blood components exerting an influence on the measurement result of the blood alcohol concentration and by measuring the blood alcohol concentration of the driver based on the absorbance detected with respect to a physical body of a user by using the plurality of selected wavelengths. Starting of the vehicle is controlled based on the blood alcohol concentration of the driver, which is measured by measuring the alcohol concentration.

20 Claims, 12 Drawing Sheets

APPARATUS AND METHOD FOR MEASURING ALCOHOL CONCENTRATION, AND SYSTEM FOR CONTROLLING STARTING OF VEHICLE

CROSS-REFERENCE TO RELATED APPLICATION

This application claims under 35 U.S.C. § 119(a) the benefit of Korean Patent Application No. 10-2019-0040256, filed in the Korean Intellectual Property Office on Apr. 5, 2019, the entire contents of which are incorporated herein by reference.

BACKGROUND

(a) Technical Field

The present disclosure relates to a technique of optically measuring the blood alcohol concentration of a driver.

(b) Description of the Related Art

Traffic accidents caused by drunk driving result in many casualties and significant economic losses every year. Ceasing operation of a vehicle after driving has already begun may not fundamentally restrict the behavior. Accordingly, some advanced countries have applied ignition interlocking devices (IIDs), which have an effect of controlling access to driving before the drunk driving takes place. The IID is a system to determine whether a driver is drunk before the driver starts a vehicle, such that the driver can be prevented from operating the vehicle if he or she is in an intoxicated state.

Currently, methods used to measure the drunken state of a driver are mainly classified into a breathing manner and a touch-based optical manner. The breathing manner measures an alcohol component included in air generated from the breath of the driver, and the alcohol component may be measured through a semiconductor manner and a fuel cell manner. Measuring the alcohol component through the breathing manner may have the possibility that a driver starts the vehicle by another person or may cause a measurement error due to other intoxicated passengers.

SUMMARY

An aspect of the present disclosure provides an apparatus and method for measuring an alcohol concentration, capable of rapidly and precisely measuring a blood alcohol concentration of a driver by selecting a plurality of wavelengths based on the absorbance for blood components exerting an influence on the measurement result of the blood alcohol concentration and by measuring the blood alcohol concentration of the driver based on the absorbance detected with respect to a physical body of a user by using the plurality of selected wavelengths.

Another aspect of the present disclosure provides a system for controlling starting of a vehicle, capable of preventing a driver from starting the vehicle through controlling the starting of the vehicle based on the blood alcohol concentration of the driver, which is measured through the above-described manner of measuring the alcohol concentration.

The technical problems to be solved by the present disclosure are not limited to the aforementioned problems, and any other technical problems not mentioned herein will be clearly understood from the following description by those skilled in the art to which the present disclosure pertains.

According to an aspect of the present disclosure, an apparatus for measuring an alcohol concentration may include a light irradiator to irradiate light having specific wavelengths to a physical body of a driver, an optical receiver configured to receive light having each of a plurality of wavelengths, which is reflected from the physical body of the driver, and a controller configured to detect an absorbance of each wavelength based on an amount of the light having the wavelength, which is received by the optical receiver, and to measure a blood alcohol concentration of the driver based on the detected absorbance of the wavelength.

In this case, the light having the specific wavelengths may be selected based on an absorbance for ethanol contained in a blood component, an absorbance for hemoglobin contained in the blood component, or an absorbance for glucose contained in the blood component.

For example, the light having the specific wavelengths may include light having a first wavelength allowing an amount of light absorbed in the ethanol to exceed a maximum threshold value, light having a second wavelength allowing the amount of the light absorbed in the ethanol not to a minimum threshold value, and light having a third wavelength allowing the amount of the light absorbed in the ethanol not to the minimum threshold value. In this case, the light having the first wavelength, the light having the second wavelength, and the light having the third wavelength satisfy the equations listed below with respect to the hemoglobin and the glucose, $$A_{1h} - A_{2h} \approx A_{2h} - A_{3h}$$

$$A_{1g} - A_{2g} \approx A_{2g} - A_{3g},$$

In the above equations, A1h denotes an absorbance of the first wavelength for the hemoglobin, A2h denotes an absorbance of the second wavelength for the hemoglobin, and A3h denotes an absorbance of the third wavelength for the hemoglobin, and wherein A1g denotes an absorbance of the first wavelength for the glucose, A2g denotes the absorbance of the second wavelength for the glucose, and A3g denotes the absorbance of the third wavelength for the glucose.

In addition, preferably, the light irradiator irradiates the light having the specific wavelengths to blood in a finger of the driver.

In addition, the light irradiator may extract the light having the specific wavelengths by filtering light irradiated from a multi-wavelength light source. In this case, the optical filter may form a first air gap when a first driving voltage is applied, form a second air gap when a second driving voltage is applied, and form a third air gap when a third driving voltage is applied. Further, the optical filter may extract light having a first wavelength from light, which is supplied from the multi-wavelength light source, through the formed first air gap, extract light having a second wavelength from light, which is supplied from the multi-wavelength light source, through the formed second air gap, and extract light having a third wavelength from light, which is supplied from the multi-wavelength light source, through the formed third air gap.

According to an aspect of the present disclosure, a method for measuring an alcohol concentration may include irradiating, by a light irradiator, light having specific wavelengths to a physical body of a driver, receiving, by an optical receiver, light having each of a plurality of wavelengths, which is reflected from the physical body of the driver, and detecting, by a controller, an absorbance of each wavelength based on an amount of the light having the wavelength, which is received, to receive a blood alcohol concentration of a driver based on the detected absorbance of the wavelength.

In this case, the light having the specific wavelengths may be selected based on an absorbance for ethanol contained in a blood component, an absorbance for hemoglobin contained in the blood component, and an absorbance for glucose contained in the blood component.

For example, the light having the specific wavelengths may include light having a first wavelength allowing an amount of light absorbed in the ethanol to exceed a maximum threshold value, light having a second wavelength allowing the amount of the light absorbed in the ethanol not to a minimum threshold value, and light having a third wavelength allowing the amount of the light absorbed in the ethanol not to the minimum threshold value. In this case, the light having the first wavelength, the light having the second wavelength, and the light having the third wavelength satisfy the equations listed below with respect to the hemoglobin and the glucose, and $$A_{1h}-A_{2h} \approx A_{2h}-A_{3h}$$

$$A_{1g}-A_{2g} \approx A_{2g}-A_{3g}$$

In the above equations, $A_{1h}$ denotes an absorbance of the first wavelength for the hemoglobin, $A_{2h}$ denotes an absorbance of the second wavelength for the hemoglobin, and $A_{3h}$ denotes an absorbance of the third wavelength for the hemoglobin, and wherein $A_{1g}$ denotes an absorbance of the first wavelength for the glucose, $A_{2g}$ denotes the absorbance of the second wavelength for the glucose, and $A_{3g}$ denotes the absorbance of the third wavelength for the glucose.

In addition, the irradiating of the light having the specific wavelengths may include irradiating the light having the specific wavelengths to blood in a finger of the driver.

According to an aspect of the present disclosure, a system, which is another device for controlling starting of a vehicle, may include a measuring device to measure a blood alcohol concentration of a driver, based on an absorbance of a specific wavelength for blood, and a control device to determine whether to allow starting of the vehicle based on the blood alcohol concentration of the driver, which is measured by the measuring device.

The another device may include a storage device to store a vein pattern, which is previously registered, of a finger of a drive, and an image sensor to photograph a vein in the finger of the driver. In this case, the storage device may store vein patterns of fingers of a plurality of drivers.

In addition, the control device may allow the starting of the vehicle when the blood alcohol concentration of the driver does not exceed a reference value, and when a vein pattern photographed by the image sensor is matched with the vein pattern stored in the storage device.

In addition, the measuring device may include a light irradiator to irradiate light having specific wavelengths to a physical body of a driver, an optical receiver to receive light having each of a plurality of wavelengths, which is reflected from the physical body of the driver, and a controller to detect an absorbance of each wavelength based on an amount of the light having the wavelength, which is received by the optical receiver, and to measure a blood alcohol concentration of a driver based on the detected absorbance of the wavelength.

In this case, the light having the specific wavelengths may be selected based on an absorbance for ethanol contained in a blood component, an absorbance for hemoglobin contained in the blood component, and an absorbance for glucose contained in the blood component.

For example, the light having the specific wavelengths may include light having a first wavelength allowing an amount of the light absorbed in the ethanol to exceed a maximum threshold value, light having a second wavelength allowing the amount of the light absorbed in the ethanol not to a minimum threshold value, and light having a third wavelength allowing the amount of the light absorbed in the ethanol not to the minimum threshold value. In this case, the light having the first wavelength, the light having the second wavelength, and the light having the third wavelength may satisfy equations listed below with respect to the hemoglobin and the glucose, $$A_{1h}-A_{2h} \approx A_{2h}-A_{3h}$$

$$A_{1g}-A_{2g} \approx A_{2g}-A_{3g}$$

In the above equations, $A_{1h}$ denotes an absorbance of the first wavelength for the hemoglobin, $A_{2h}$ denotes an absorbance of the second wavelength for the hemoglobin, and $A_{3h}$ denotes an absorbance of the third wavelength for the hemoglobin, and $A_{1g}$ denotes an absorbance of the first wavelength for the glucose, $A_{2g}$ denotes the absorbance of the second wavelength for the glucose, and $A_{3g}$ denotes the absorbance of the third wavelength for the glucose.

In addition, the light irradiator may irradiate the light having the specific wavelengths to blood in a finger of the driver.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
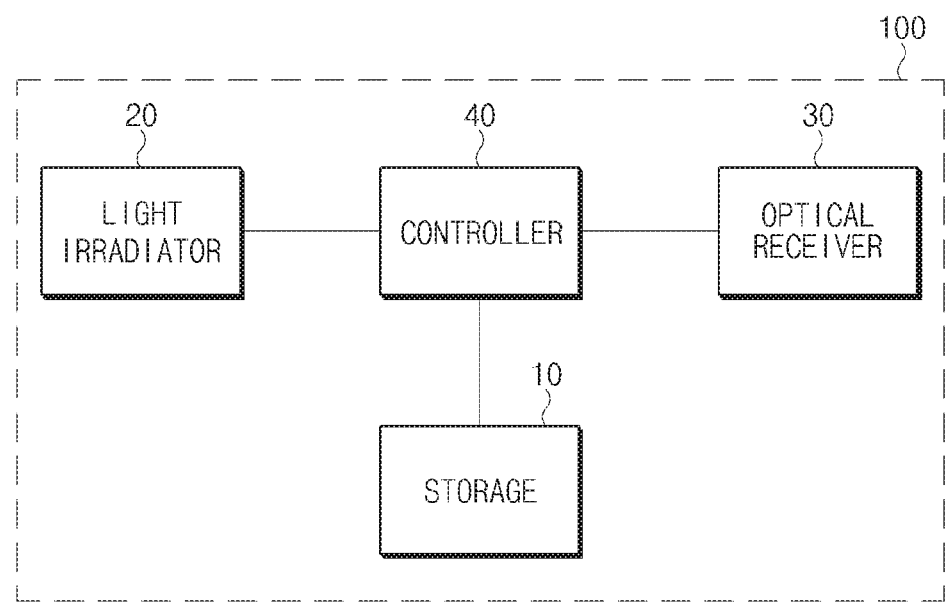
FIG. 1 is a block diagram illustrating an apparatus for measuring an alcohol concentration, according to an embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the embodiment of the present disclosure, a detailed description of well-known features or functions will be ruled out in order not to unnecessarily obscure the gist of the present disclosure.

In describing the components of the embodiment according to the present disclosure, terms such as first, second, "A", "B", (a), (b), and the like may be used. These terms are merely intended to distinguish one component from another component, and the terms do not limit the nature, sequence or order of the constituent components. In addition, unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

In the present disclosure, the starting of the vehicle has a concept including not only the starting of an internal combustion engine, but also for the starting (running preparation) of an electric vehicle. In other words, the present disclosure may apply to all types of vehicles including an electric vehicle, a hybrid vehicle, and a fuel cell vehicle.

FIG. 1 is a block diagram illustrating an apparatus for measuring an alcohol concentration, according to an embodiment of the present disclosure, and illustrates an apparatus for optically measuring the alcohol concentration.

As illustrated in FIG. 1, according to an embodiment of the present disclosure, the apparatus 100 for measuring the alcohol concentration may include a storage 10, a light irradiator 20, an optical receiver 30, and a controller 40. In this case, according to an embodiment of the present disclosure, the above components may be integrated into each other to be implemented in one body, or some of the above components may be omitted, depending on implementation of the apparatus 100 for measuring the alcohol concentration.

Hereinafter, the details of each component will be described. The storage 10 may store various logic, algorithms, and programs required to select a plurality of wavelengths based on absorbance for blood components affecting the measurement result of blood alcohol concentration, or to measure the blood alcohol concentration of a driver based on the absorbance detected using the plurality of wavelengths selected for a physical body of the driver.

In addition, the storage 10 may further store a table having absorbance corresponding to an amount of light (electric signal) received by the optical receiver 30.

In addition, the storage 10 may be implemented with at least one storage medium of a memory in a flash memory type, a hard disk type, a micro type, the type of a card (e.g., a Security Digital (SD) card or an eXtreme digital card), a Random Access Memory (RAM), a Static RAM (SRAM), a Read Only Memory (ROM), a Programmable ROM (PROM), an Electrically Erasable and Programmable ROM (EEPROM), a magnetic RAM (MRAM), a magnetic disk-type memory, and an optical disk-type memory.

The light irradiator 20 irradiates light having specific wavelengths to the physical body of the driver. In other words, the light irradiator 20 irradiates light having the specific wavelengths to the blood in the capillary blood vessels of the driver. In this case, a designer may select light having a specific wavelength based on the absorbance for blood components affecting the measurement result of the blood alcohol concentration. In this case, the blood components affecting the measurement result of the blood alcohol concentration may include hemoglobin and glucose.

The designer selects the specific wavelengths by first selecting the first wavelength (e.g., 1700 nm) the most absorbed into ethanol and selecting a second wavelength and a third wavelength less absorbed into ethanol than the first wavelength. The first wavelength, the second wavelength, and the third wavelength have to satisfy the following Equation 1 with respect to hemoglobin while satisfying the following Equation 2 with respect to glucose. In this case, the first wavelength may refer to a wavelength allowing an amount of light, which is absorbed into ethanol, to exceed the maximum threshold value, and the second wavelength and the third wavelength allowing an amount of the light, which is absorbed in ethanol, not to the minimum threshold value.

$$A_{1h}-A_{2h} \approx A_{2h}-A_{3h} \quad \text{[Equation 1]}$$

In Equation 1, $A_{1h}$ denotes the absorbance of the first wavelength for hemoglobin, $A_{2h}$ denotes the absorbance of the second wavelength for the hemoglobin, and $A_{3h}$ denotes the absorbance of the third wavelength for the hemoglobin.

$$A_{1g}-A_{2g} \approx A_{2g}-A_{3g} \quad \text{[Equation 2]}$$

In Equation 2, $A_{1g}$ denotes the absorbance of the first wavelength for glucose, $A_{2g}$ denotes the absorbance of the second wavelength for glucose, and $A_{3g}$ denotes the absorbance of the third wavelength for glucose.

The optical receiver 30 receives light having each of a plurality of wavelengths, which are irradiated by the light irradiator 20 and reflected from the physical body of the driver. In other words, the optical receiver 30 receives light having specific wavelengths irradiated by the light irradiator 20 are reflected from the blood in the capillary blood vessel of the driver.

In addition, the optical receiver 30 may transmit an electric signal corresponding to an amount of light of each wavelength which is received.

Hereinafter, the configuration and the structure of the light irradiator 20 and the optical receiver 30 will be described with reference to FIGS. 2 and 3.

Figure 2:
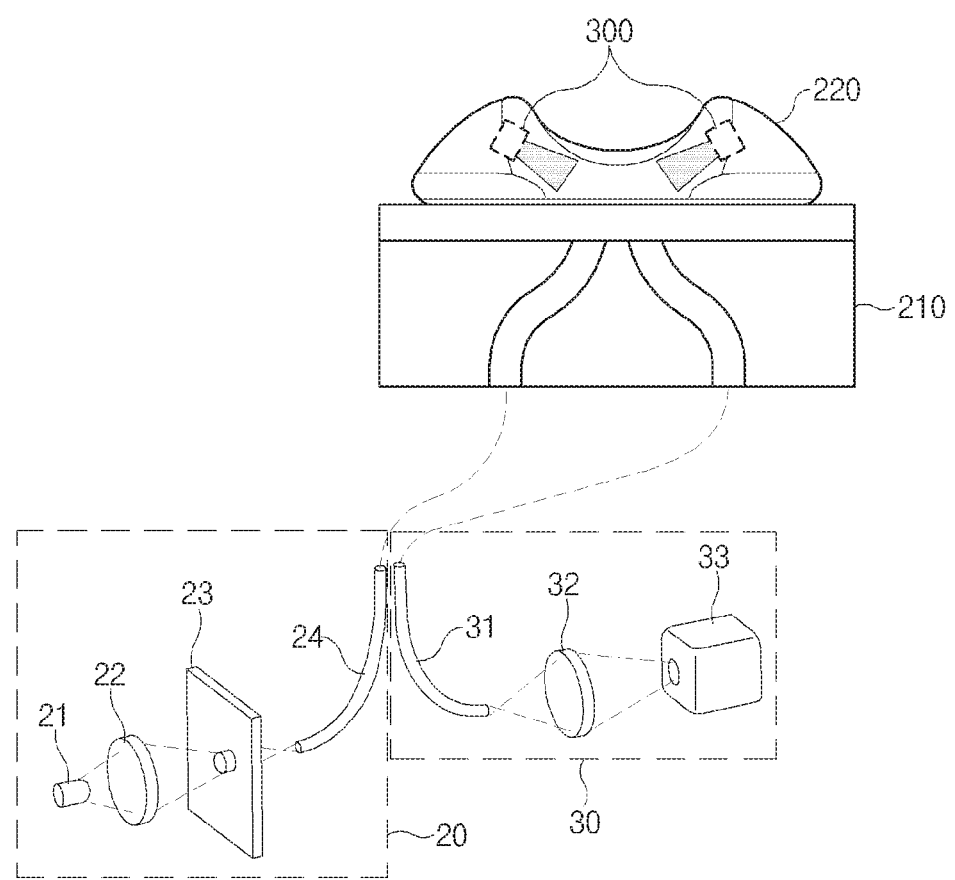
FIG. 2 is a view illustrating the configurations of a light irradiator and an optical receiver of an apparatus for measuring an alcohol concentration, according to an embodiment of the present disclosure.

FIG. 2 is a view illustrating the configurations of the light irradiator and the optical receiver of the apparatus for measuring the alcohol concentration, according to an embodiment of the present disclosure.

As illustrated in FIG. 2, the light irradiator 20 may include a multi-wavelength light source 21, a lens 22, a Micro Electro Mechanical Systems (MEMS) optical filter 23, and an optical fiber 24.

The multi-wavelength light source 21 irradiates light having mutually different wavelengths.

The lens 22 may transmit light, which is irradiated from the multi-wavelength light source 21, to the MEMS optical filter 23.

The MEMS optical filter 23 filters light irradiated from the multi-wavelength light source 21 to extract the light having the first wavelength, the light having the second wavelength, and the light having the third wavelength.

Such a MEMS optical filter 23 may be used to measure the concentration of blood glucose. In other words, the MEMS optical filter 23 may extract the light having a wavelength of 8 µm to 10 µm used for measuring the concentration of blood glucose.

The optical fiber 24 transmits the light of the first wavelength, the light of the second wavelength, and the light of the third wavelength, which are extracted by the MEMS optical filter 23, to the finger of the diver.

As illustrated in FIG. 2, the optical receiver 30 may include an optical fiber 31, a lens 32, and a light receiving sensor 33.

The optical fiber 31 transmits the light, which is reflected from the capillary blood of the finger of the driver, to the lens 32

The lens 32 transmits light, which is received from the optical fiber 31, to the light receiving sensor 33.

The light receiving sensor 33 transmits, to the controller 40, an electric signal corresponding to an amount of light input through the lens 32

Figure 3:
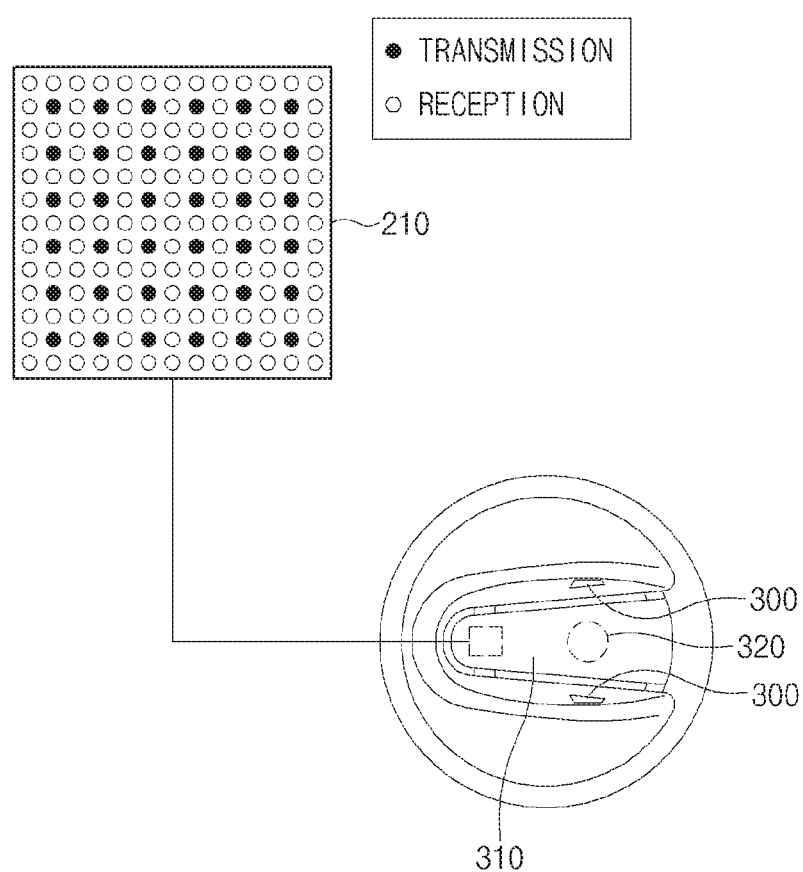
FIG. 3 is a view illustrating a finger seating member of an apparatus for measuring an alcohol concentration, according to an embodiment of the present disclosure.

Meanwhile, the optical fiber 24 of the light irradiator 20 and the optical fiber 31 of the optical receiver 30 may be configured in plural, and an end of a plurality of optical fibers 24 and an end of a plurality of optical fibers 31 may be implemented in the form of passing through a rectangular pad 210 as illustrated in FIG. 3. In this case, the number of optical fibers 31, which passes through the pad 210, of the optical receiver 30 is larger than the number of the optical fibers 24, which passes through the pad 210, of the light irradiator 20 passing through the pad 210. As the pad 210 is positioned on a surface touched by a finger of the driver, the optical fiber 24 may irradiate light into the capillary blood in the finger and the optical fiber 31 may receive light reflected by the capillary blood of the finger. For example, the width of the pad 210 may be 5 mm, and the length of the pad 210 may be 5 mm.

A member 220 to guide the touch position of the finger may have a height corresponding to the height of the finger, and optical transmitters 300 may be provided on both sides of the member 220 to transmit the light to the finger. For example, the member 220 may be implemented in the shape of a circle having a diameter of 50 mm. In this case, an optical splitter (not illustrated) may transmit light, which is irradiated from the optical fiber 24 of the light irradiator 20, to the optical transmitters 300 under the control of the control device 400.

In addition, when light is transmitted through the optical transmitter 300, the control device 400 may control an image sensor 320 to photograph the vein in the finger.

The controller 40 performs the overall control operation such that the components normally perform the intrinsic functions thereof. In addition, the controller 40 may be implemented in the form of hardware or software, or may be implemented in the form of a combination of hardware and software. Preferably, the controller 40 may be implemented in the form of a micro-processor, but the present disclosure is not limited thereto.

The controller 40 may perform various control operations while detecting the absorbance for the blood in the finger of the driver using the plurality of wavelengths which are previously selected and measuring the blood alcohol concentration of the driver based on a plurality of absorbance values which are detected.

The controller 40 may control the light irradiator 20 such that light having a plurality of wavelengths are irradiated to the capillary blood of the finger of the driver, when the finger of the driver is seated on a finger seating member 310. In this case, the controller 40 may determine whether the finger is seated, using a sensor (not illustrated).

The controller 40 may control the optical receiver 30 to receive light having each wavelength, which is reflected from the capillary blood of the finger, and to output an electric signal corresponding to an amount of the received light having the wavelength.

The controller 40 may detect the absorbance corresponding to the electric signal for each wavelength, which is output from the optical receiver 30, and may measure the blood alcohol concentration of the driver, based on the absorbance for each wavelength. In this case, the controller 40 may measure the blood alcohol concentration D based on the following Equation 3.

$$D = \frac{\sum (A_{1b} - A_{2b})}{\sum (A_{2b} - A_{3b})} \quad \text{[Equation 3]}$$

In Equation 3, $A_{1b}$ denotes the absorbance of the first wavelength for the blood, $A_{2b}$ denotes the absorbance of the second wavelength for the blood, and $A_{3b}$ denotes the absorbance of the third wavelength for the blood.

Figure 4A:
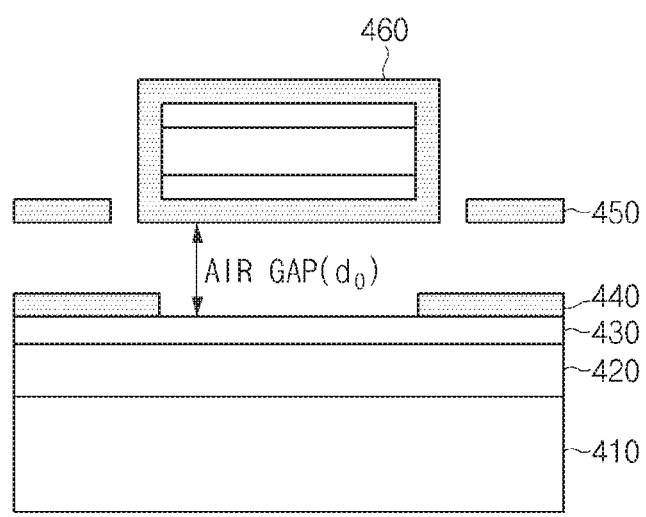
FIG. 4A illustrates an MEMS optical filter provided in a light irradiator of an apparatus for measuring an alcohol concentration, according to an embodiment of the present disclosure.

FIG. 4A illustrates an MEMS optical filter provided in the light irradiator of the apparatus for measuring the alcohol concentration, according to an embodiment of the present disclosure.

In FIG. 4A, reference numeral 410 may be implemented with silicon, reference numeral 420 may be implemented with silicon monoixide, and reference numeral may be implemented with germanium. In addition, reference numeral 440 represents a lower electrode, reference numeral 450 represents an upper electrode, and reference numeral 460 represents a dielectric mirror.

An air gap do between the lower electrode 440 and the upper electrode 450 is a factor to exert an influence on filtering light having a specific wavelength of multiple wavelengths, and the details thereof will be described with reference to FIGS. 4B to 4E.

FIGS. 4B to 4E are views illustrating the operation of the MEMS optical filter provided in the light irradiator of the apparatus for measuring the alcohol concentration according to an embodiment of the present disclosure.

Figure 4B:
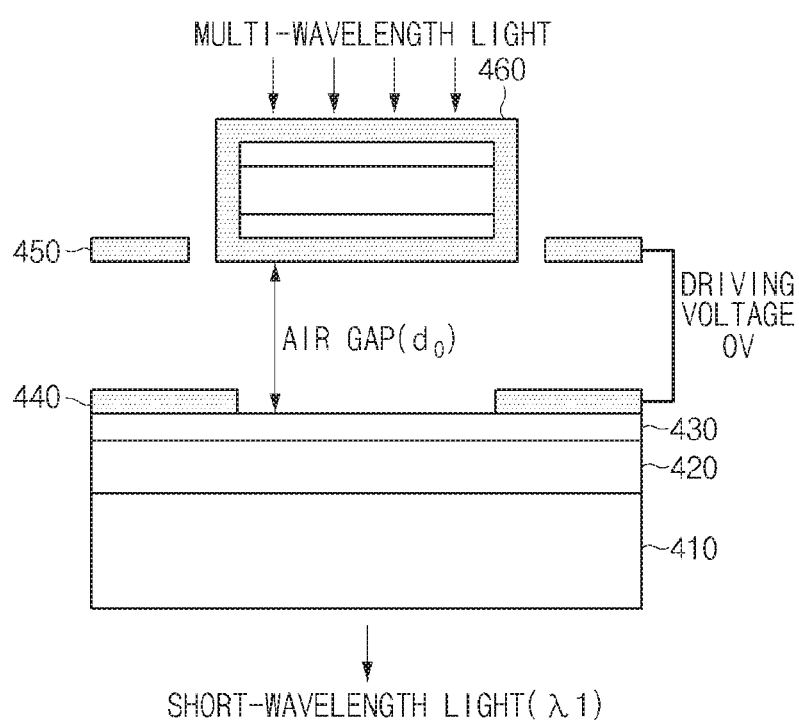
FIGS. 4B to 4E are views illustrating the operation of an MEMS optical filter provided in a light irradiator of than apparatus for measuring an alcohol concentration according to an embodiment of the present disclosure.

FIG. 4B illustrates the procedure of extracting the light having the first wavelength $\lambda_1$ from the light having multiple wavelengths, due to the air gap do corresponding to the driving voltage of 0V, when the driving voltage of 0V is applied between the lower electrode 440 and the upper electrode 450 of the MEMS optical filter 23.

Figure 4C:
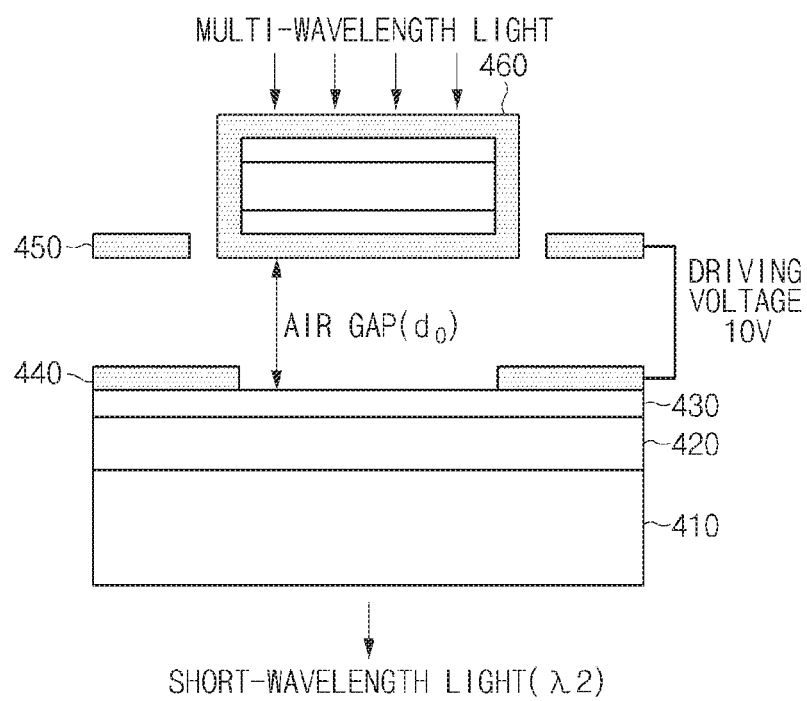

FIG. 4C illustrates the procedure of extracting the light having the second wavelength $\lambda_2$ from the light having multiple wavelengths, due to the air gap do corresponding to the driving voltage of 10V, when the driving voltage of 10V is applied between the lower electrode 440 and the upper electrode 450 of the MEMS optical filter 23.

Figure 4D:
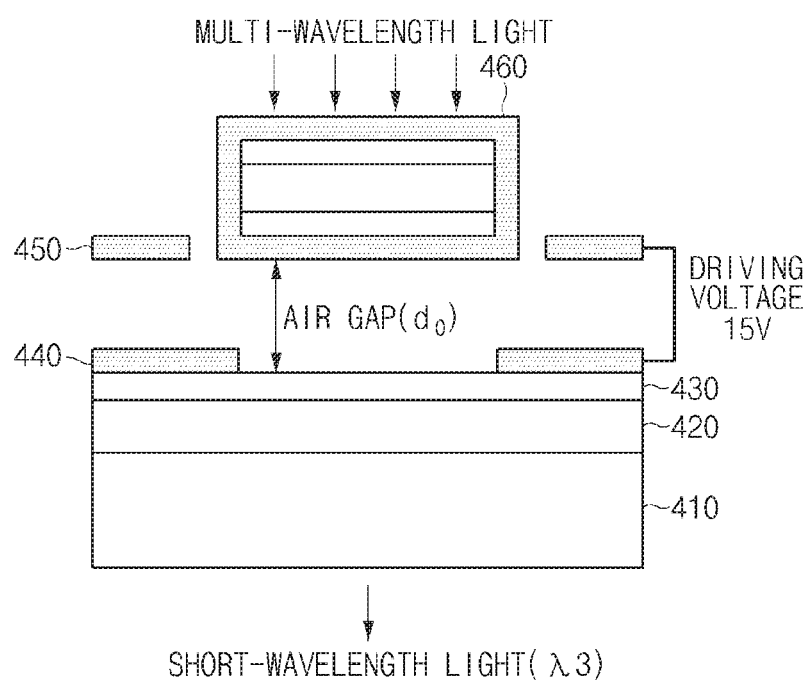

FIG. 4D illustrates the procedure of extracting light having the third wavelength $\lambda_3$ from light having multiple wavelengths, due to the air gap do corresponding to the driving voltage of 15V, when the driving voltage of 15V is applied between the lower electrode 440 and the upper electrode 450 of the MEMS optical filter 23.

Figure 4E:
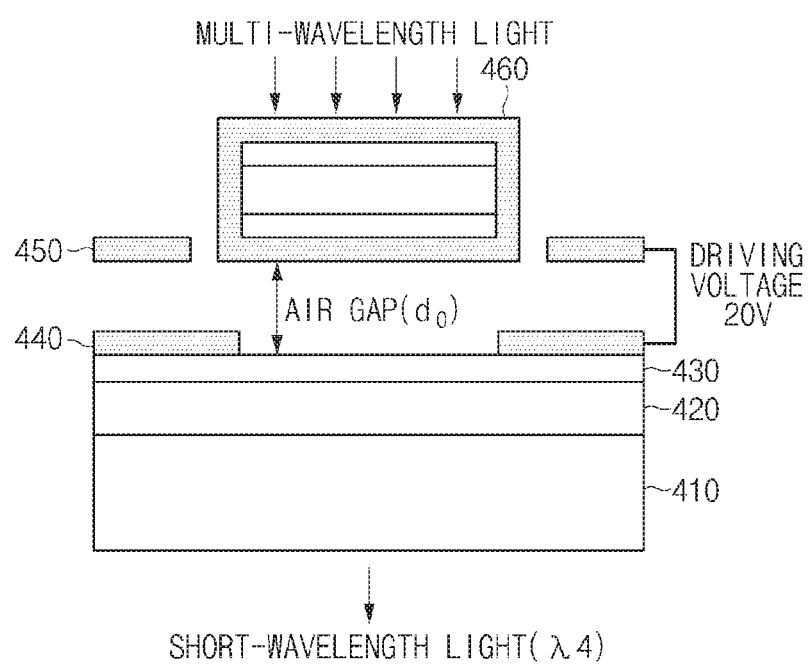

FIG. 4E illustrates the procedure of extracting light having the fourth wavelength $\lambda_4$ from light having multiple wavelengths, due to the air gap do corresponding to the driving voltage of 20V, when the driving voltage of 20V is applied between the lower electrode 440 and the upper electrode 450 of the MEMS optical filter 23.

Referring to FIGS. 4B to 4E, as the driving voltage applied to the MEMS optical filter 23 is increased, the air gap may be reduced.

Accordingly, the controller 40 may extract the light having the first wavelength, the light having the second wavelength, and the light having the third wavelength by controlling the driving voltage applied to the MEMS optical filter 23 of the light irradiator 20.

In other words, the controller 40 may extract the light having the first wavelength by applying a first driving voltage to the MEMS optical filter 23 of the light irradiator 20. In this case, the MEMS optical filter 23 may form the first air gap corresponding to the first driving voltage and may extract the light having the first wavelength through the first air gap.

In addition, the controller 40 may extract the light having the second wavelength by applying a second driving voltage to the MEMS optical filter 23 of the light irradiator 20. In this case, the MEMS optical filter 23 may form the second air gap corresponding to the second driving voltage and may extract the light having the second wavelength through the second air gap.

In addition, the controller 40 may extract the light having the third wavelength by applying a third driving voltage to the MEMS optical filter 23 of the light irradiator 20. In this case, the MEMS optical filter 23 may form the third air gap corresponding to the third driving voltage and may extract the light having the third wavelength through the third air gap.

Accordingly, the controller 40 may extract the light having a specific wavelength used to measure the blood alcohol concentration of the driver by adjusting the driving voltage applied to the MEMS optical filter 23 of the light irradiator 20.

According to another embodiment, the controller 40 may extract light having a specific wavelength, which is in the range of 8 to 10 μm, used to measure the blood glucose concentration of the driver by adjusting the driving voltage applied to the MEMS optical filter 23 of the light irradiator 20.

In other words, the controller 40 may control the light irradiator 20 such that light having a specific wavelength, which is in the range of 8 to 10 μm, is irradiated to the capillary blood of the finger of the driver, when the finger of the driver is positioned on the finger seating member 310. In addition, the controller 40 controls the light irradiator 20 to receive the light having the wavelength reflected from the capillary blood of the finger and to output an electric signal corresponding to an amount of the light having the wavelength. The controller 40 may detect the absorbance corresponding to the electric signal for each wavelength, which is output from the optical receiver 30, and may measure the blood glucose concentration of the driver, based on the absorbance for each wavelength.

Figure 4F:
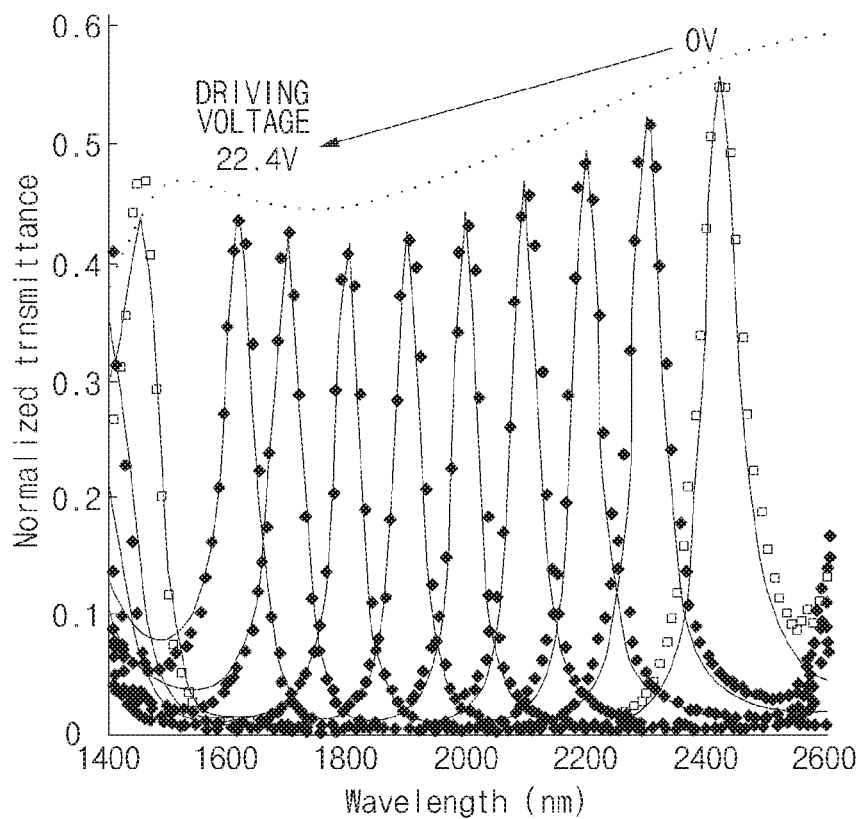
FIG. 4F is a graph illustrating the performance analysis of an MEMS optical filter provided in a light irradiator of an apparatus for measuring an alcohol concentration, according to an embodiment of the present disclosure.

FIG. 4F is a graph illustrating the performance analysis of the MEMS optical filter provided in the light irradiator of the apparatus for measuring the alcohol concentration, according to an embodiment of the present disclosure.

As illustrated in FIG. 4F, a horizontal axis represents the wavelength nm and the vertical axis represents a normalized transmittance. Accordingly, it can be recognized that the MEMS optical filter 23 extracts light having mutually different wavelengths depending on the applied driving voltages 0V to 22.4V.

Meanwhile, the relationship between the air gap do and the wavelength of the filtered light satisfies the following Equation 4.

$$d_0 = \frac{m \times \lambda}{2} \qquad \text{[Equation 4]}$$

In Equation 4, "m" represents an interference order and "λ" represents the wavelength of the filtered light.

Figure 5:
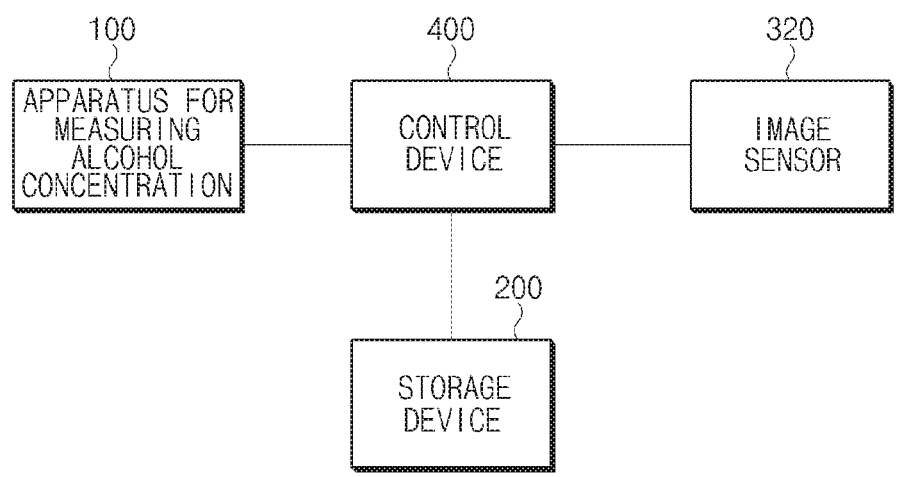
FIG. 5 is a block diagram illustrating a system for controlling the starting of a vehicle, according to an embodiment of the present disclosure.

FIG. 5 is a block diagram illustrating a system for controlling the starting of the vehicle, according to an embodiment of the present disclosure.

As illustrated in FIG. 5, according to an embodiment of the present disclosure, the system for controlling the starting of the vehicle may include the apparatus 100 for measuring the alcohol concentration, a storage device 200, an image sensor 320, and a control device 400.

Regarding the components, the storage device 200 store a vein pattern, which is previously registered, of a finger of a driver. In this case, a plurality of drivers may be previously registered.

The image sensor 320 may be positioned on the surface of the finger seating member 310 for seating the finger of the driver to photograph the vein inside the finger.

The controller 40 performs the overall control such that the components normally perform the respective functions. In addition, the controller 40 may be implemented in the form of hardware or software, and may be implemented in the form of the combination of the hardware and the software. Preferably, the controller 40 may be implemented in the form of a micro-processor, but the present disclosure is not limited thereto.

The control device 400 may determine whether the starting of the vehicle is allowed, based on the blood alcohol concentration, which is measured by the apparatus 100 for measuring the alcohol concentration, of the driver. In other words, the control device 400 prevents the starting of the vehicle when the blood alcohol concentration of the driver exceeds a reference value, and allows the starting of the vehicle when the blood alcohol concentration of the driver does not exceed the reference value. Accordingly, when the driver is drunk, the driver is prevented from starting the vehicle, thereby fundamentally preventing the driver from driving in the drunken state.

The control device 400 may determine whether the starting of the vehicle is allowed, by determining whether the driver is allowed to drive the vehicle. In other words, the control device 400 may determine whether the starting of the vehicle is allowed by further determining whether the driver is allowed to drive the vehicle (whether the driver is previously registered), without instantly allowing the starting of the vehicle when the blood alcohol concentration of the driver does not exceed a reference value. In this case, when the control device 400 determines the driver as being allowed to drive the vehicle when the vein pattern photographed by the image sensor 320 is matched with the vein pattern, which is stored in the storage device 200 and is previously registered, of the finger of the driver. The technique of determining the similarity may be applied to the procedure of determining the matching state of the vein pattern.

Figure 6:
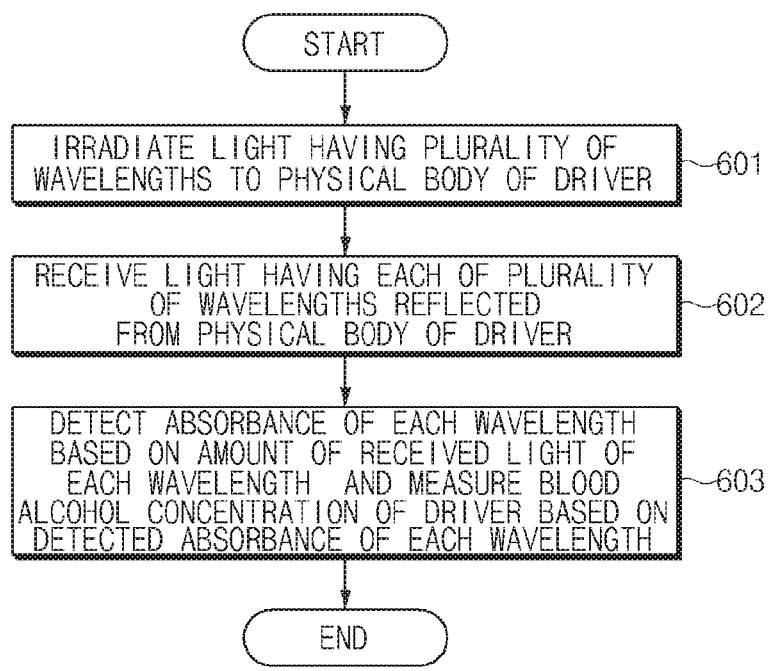
FIG. 6 is a flowchart illustrating a method for measuring AN alcohol concentration, according to an embodiment of the present disclosure.

FIG. 6 is a flowchart illustrating a method for measuring the alcohol concentration, according to an embodiment of the present disclosure.

First, the light irradiator 20 irradiates light having specific wavelengths to the physical body of the driver (601). In this case, the light irradiator 20 may irradiate light when the finger of the driver is seated on the finger seating member 310.

Thereafter, the optical receiver 30 receives the light having the wavelength reflected from the physical body of the driver (602).

Thereafter, the controller 40 detects the absorbance of each wavelength based on an amount of light having the wavelength, which is received by the light irradiator 20, and measures the blood alcohol concentration of the driver based on the detected absorbance of each wavelength (603).

Figure 7:
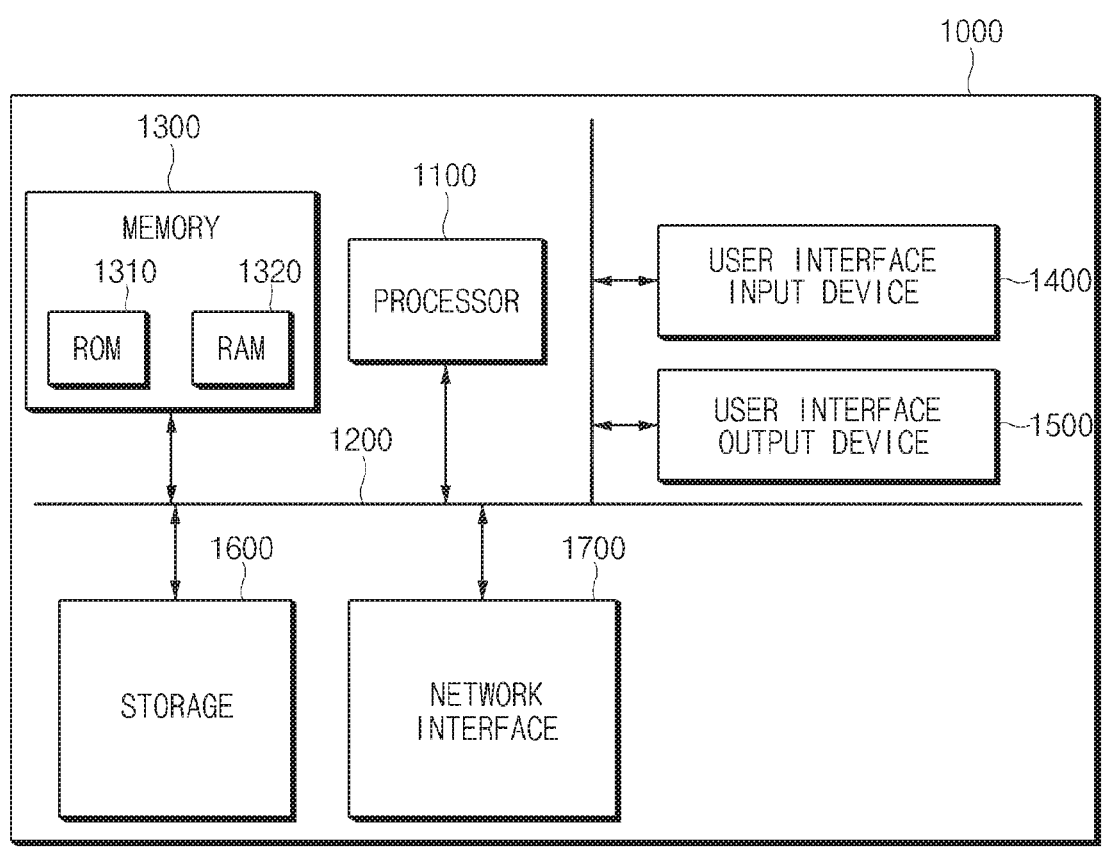
FIG. 7 is a block diagram illustrating a computing system to execute a method for measuring an alcohol concentration, according to an embodiment of the present disclosure.

FIG. 7 is a block diagram illustrating a computing system to execute the method for measuring the alcohol concentration, according to an embodiment of the present disclosure.

Referring to FIG. 7, according to an embodiment of the present disclosure described above, the method for measuring the alcohol concentration may be implemented through the computing system. A computing system 1000 may include at least one processor 1100, a memory 1300, a user interface input device 1400, a user interface output device 1500, a storage 1600, and a network interface 1700, which are connected with each other via a system bus 1200.

The processor 1100 may be a central processing unit (CPU) or a semiconductor device for processing instructions stored in the memory 1300 and/or the storage 1600. Each of the memory 1300 and the storage 1600 may include various types of volatile or non-volatile storage media. For example, the memory 1300 may include a read only memory (ROM) and a random access memory (RAM).

Thus, the operations of the methods or algorithms described in connection with the embodiments disclosed in the present disclosure may be directly implemented with a hardware module, a software module, or the combinations thereof, executed by the processor 1100. The software module may reside on a storage medium (i.e., the memory 1300 and/or the storage 1600), such as a RAM, a flash memory, a ROM, an erasable and programmable ROM (EPROM), an electrically EPROM (EEPROM), a register, a hard disc, a removable disc, or a compact disc-ROM (CD-ROM). The exemplary storage medium may be coupled to the processor 1100. The processor 1100 may read out information from the storage medium and may write information in the storage medium. Alternatively, the storage medium may be integrated with the processor 1100. The processor and storage medium may reside in an application specific integrated circuit (ASIC). The ASIC may reside in a user terminal. Alternatively, the processor and storage medium may reside as separate components of the user terminal.

According to an embodiment of the present disclosure, in the apparatus for measuring the alcohol concentration and the method for the same, the blood alcohol concentration of the driver may be rapidly and significantly precisely measured by selecting a plurality of wavelengths based on the absorbance for the blood components exerting the influence on the measurement result of the blood alcohol concentration and by measuring the blood alcohol concentration of the driver based on the absorbance detected with respect to a physical body of the user by using the plurality of selected wavelengths.

In addition, according to an embodiment of the present disclosure, in the system for controlling the starting of the vehicle, the driver may be fundamentally prevented from driving the vehicle in the drunken state by preventing the drunken driver from starting the vehicle through controlling the starting of the vehicle based on the blood alcohol concentration of the driver, which is measured through the above-described manner of measuring the alcohol concentration.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, exemplary embodiments of the present disclosure are not limiting, but illustrative, and the spirit and scope of the present disclosure is not limited thereto. The spirit and scope of the present disclosure should be interpreted by the following claims, and it should be interpreted that all technical ideas which are equivalent to the present disclosure are included in the spirit and scope of the present disclosure.

What is claimed is:
1. An apparatus for measuring an alcohol concentration, the apparatus comprising:
a light irradiator configured to irradiate light having specific wavelengths to a physical body of a driver;

an optical receiver configured to receive light having each of the specific wavelengths, which is reflected from the physical body of the driver; and a controller configured to detect an absorbance of each of the specific wavelengths based on an amount of the light having the wavelength, which is received by the optical receiver, and to measure a blood alcohol concentration of the driver based on the detected absorbance of the specific wavelengths;

wherein the light having the specific wavelengths is selected based on an absorbance for ethanol contained in a blood component, an absorbance for hemoglobin contained in the blood, and an absorbance for glucose contained in the blood.

2. The apparatus of claim 1, wherein the light having the specific wavelengths includes:

light having a first wavelength allowing an amount of light absorbed in the ethanol to exceed a maximum threshold value;

light having a second wavelength allowing the amount of the light absorbed in the ethanol not to a minimum threshold value; and light having a third wavelength allowing the amount of the light absorbed in the ethanol not to the minimum threshold value.

3. The apparatus of claim 2, wherein the light having the first wavelength, the light having the second wavelength, and the light having the third wavelength satisfy equations listed below with respect to the hemoglobin and the glucose:

$$A_{1h}-A_{2h} \cong A_{2h}-A_{3h}$$

$$A_{1g}-A_{2g} \cong A_{2g}-A_{3g}$$

wherein $A_{1h}$ denotes an absorbance of the first wavelength for the hemoglobin, $A_{2h}$ denotes an absorbance of the second wavelength for the hemoglobin, and $A_{3h}$ denotes an absorbance of the third wavelength for the hemoglobin, and wherein $A_{1g}$ denotes an absorbance of the first wavelength for the glucose, $A_{2g}$ denotes the absorbance of the second wavelength for the glucose, and $A_{3g}$ denotes the absorbance of the third wavelength for the glucose.

4. The apparatus of claim 1, wherein the light irradiator irradiates the light having the specific wavelengths to blood in a finger of the driver.

5. The apparatus of claim 1, wherein the light irradiator extracts the light having the specific wavelengths by filtering light irradiated from a multi-wavelength light source.

6. The apparatus of claim 5, wherein the light irradiator comprises an optical filter that forms a first air gap when a first driving voltage is applied, forms a second air gap when a second driving voltage is applied, and forms a third air gap when a third driving voltage is applied.

7. The apparatus of claim 6, wherein the optical filter extracts light having a first wavelength from light, which is supplied from the multi-wavelength light source, through the formed first air gap, extracts light having a second wavelength from light, which is supplied from the multi-wavelength light source, through the formed second air gap, and extracts light having a third wavelength from light, which is supplied from the multi-wavelength light source, through the formed third air gap.

8. A method for measuring an alcohol concentration, the method comprising:

irradiating, by a light irradiator, light having specific wavelengths to a physical body of a driver;

receiving, by an optical receiver, light having each of the specific wavelengths, which is reflected from the physical body of the driver; and detecting, by a controller, an absorbance of each of the specific wavelengths based on an amount of the light having the wavelength, which is received, to measure a blood alcohol concentration of a driver based on the detected absorbance of the specific wavelengths;

wherein the light having the specific wavelengths is selected based on an absorbance for ethanol contained in a blood component, an absorbance for hemoglobin contained in the blood component, and an absorbance for glucose contained in the blood component.

9. The method of claim 8, wherein the light having the specific wavelengths includes:

light having a first wavelength allowing an amount of light absorbed in the ethanol to exceed a maximum threshold value;

light having a second wavelength allowing the amount of the light absorbed in the ethanol not to a minimum threshold value; and light having a third wavelength allowing the amount of the light absorbed in the ethanol not to the minimum threshold value.

10. The method of claim 9, wherein the light having the first wavelength, the light having the second wavelength, and the light having the third wavelength satisfy equations listed below with respect to the hemoglobin and the glucose:

$$A_{1h}-A_{2h} \cong A_{2h}-A_{3h}$$

$$A_{1g}-A_{2g} \cong A_{2g}-A_{3g}$$

wherein $A_{1h}$ denotes an absorbance of the first wavelength for the hemoglobin, $A_{2h}$ denotes an absorbance of the second wavelength for the hemoglobin, and $A_{3h}$ denotes an absorbance of the third wavelength for the hemoglobin, and wherein $A_{1g}$ denotes an absorbance of the first wavelength for the glucose, $A_{2g}$ denotes the absorbance of the second wavelength for the glucose, and $A_{3g}$ denotes the absorbance of the third wavelength for the glucose.

11. The method of claim 8, wherein the irradiating of the light having the specific wavelengths includes:

irradiating the light having the specific wavelengths to blood in a finger of the driver.

12. A system for controlling starting of a vehicle, the system comprising:

a measuring device configured to measure a blood alcohol concentration of a driver, based on absorbance of specific wavelengths for blood; and a control device configured to determine whether to allow starting of the vehicle based on the blood alcohol concentration of the driver, which is measured by the measuring device;

wherein the absorbance of specific wavelengths for blood includes an absorbance for ethanol contained in a blood component, an absorbance for hemoglobin contained in the blood component, and an absorbance for glucose contained in the blood component.

13. The system of claim 12, further comprising:

a storage device configured to store a vein pattern, which is previously registered, of a finger of a driver; and an image sensor to photograph a vein in the finger of the driver.

14. The system of claim 13, wherein the storage device stores vein patterns of fingers of a plurality of drivers.

15. The system of claim 13, wherein the control device allows the starting of the vehicle when the blood alcohol concentration of the driver does not exceed a reference value, and when a vein pattern photographed by the image sensor is matched with the vein pattern stored in the storage device.

16. The system of claim 12, wherein the measuring device includes:
- a light irradiator configured to irradiate light having the specific wavelengths to a physical body of a driver;
- an optical receiver configured to receive light having each of the specific wavelengths, which is reflected from the physical body of the driver; and
- a controller configured to detect an absorbance of each of the specific wavelengths based on an amount of the light having the wavelength, which is received by the optical receiver, and to measure a blood alcohol concentration of a driver based on the detected absorbance of the specific wavelengths.

17. The system of claim 16, wherein the light having the specific wavelengths is selected based on the absorbance for ethanol contained in the blood component, the absorbance for hemoglobin contained in the blood component, and the absorbance for glucose contained in the blood component.

18. The system of claim 17, wherein the light having the specific wavelengths includes:
- light having a first wavelength allowing an amount of the light absorbed in the ethanol to exceed a maximum threshold value;
- light having a second wavelength allowing the amount of the light absorbed in the ethanol not to a minimum threshold value; and
- light having a third wavelength allowing the amount of the light absorbed in the ethanol not to the minimum threshold value.

19. The system of claim 18, wherein the light having the first wavelength, the light having the second wavelength, and the light having the third wavelength satisfy equations listed below with respect to the hemoglobin and the glucose:

$$A_{1h} - A_{2h} \cong A_{2h} - A_{3h}$$

$$A_{1g} - A_{2g} \cong A_{2g} - A_{3g}$$

wherein, $A_{1h}$ denotes an absorbance of the first wavelength for the hemoglobin, $A_{2h}$ denotes an absorbance of the second wavelength for the hemoglobin, and $A_{3h}$ denotes an absorbance of the third wavelength for the hemoglobin, and wherein $A_{1g}$ denotes an absorbance of the first wavelength for the glucose, $A_{2g}$ denotes the absorbance of the second wavelength for the glucose, and $A_{3g}$ denotes the absorbance of the third wavelength for the glucose.

20. The system of claim 16, wherein the light irradiator irradiates the light having the specific wavelengths to blood in a finger of the driver.

* * * * *